(12) United States Patent
Hastings et al.

(10) Patent No.: US 6,607,580 B1
(45) Date of Patent: Aug. 19, 2003

(54) SEPARATION COLUMN FOR A GAS CHROMATOGRAPH

(75) Inventors: Mitchell R. Hastings, El Dorado Hills, CA (US); Allen K. Vickers, Folsom, CA (US); Gary F. Lee, Cameron Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/090,191

(22) Filed: Mar. 4, 2002

(51) Int. Cl.[7] .............................................. B01D 15/08
(52) U.S. Cl. .............................................. 95/87; 96/101
(58) Field of Search ........................... 73/23.39; 95/87; 96/101–103; 219/201, 547

(56) References Cited

U.S. PATENT DOCUMENTS

| | | | | |
|---|---|---|---|---|
| 2,864,928 A | * | 12/1958 | Danford | 219/536 |
| 2,922,866 A | * | 1/1960 | Hicks | 219/546 |
| 3,149,941 A | * | 9/1964 | Barnitz et al. | 96/101 |
| 3,225,520 A | * | 12/1965 | Burow | 95/87 |
| 3,225,521 A | * | 12/1965 | Burow | 95/86 |
| 3,630,006 A | * | 12/1971 | Sandoval | 96/101 |
| 4,350,586 A | * | 9/1982 | Conlon et al. | 210/149 |
| 4,440,013 A | * | 4/1984 | Adams | 73/23.37 |
| 4,726,822 A | * | 2/1988 | Cates et al. | 96/101 |
| 4,830,595 A | * | 5/1989 | Bentivoglio et al. | 425/143 |
| 4,891,120 A | * | 1/1990 | Sethi et al. | 204/600 |
| 4,923,486 A | * | 5/1990 | Rubey | 95/87 |
| 5,165,292 A | * | 11/1992 | Prohaska | 73/866 |
| 5,588,988 A | * | 12/1996 | Gerstel et al. | 96/101 |
| 5,601,785 A | * | 2/1997 | Higdon | 422/103 |
| 5,782,964 A | * | 7/1998 | Mustacich | 96/102 |
| 5,792,943 A | * | 8/1998 | Craig | 73/61.52 |
| 5,808,178 A | * | 9/1998 | Rounbehler et al. | 73/23.39 |
| 5,856,616 A | * | 1/1999 | Maswadeh et al. | 73/23.42 |
| 5,939,614 A | * | 8/1999 | Walters et al. | 73/23.39 |
| 5,954,860 A | * | 9/1999 | Gordon | 95/87 |
| 5,965,046 A | * | 10/1999 | Franklin et al. | 219/201 |
| 5,997,708 A | * | 12/1999 | Craig | 204/601 |
| 6,029,498 A | * | 2/2000 | Walters et al. | 73/23.39 |
| 6,068,604 A | * | 5/2000 | Krause et al. | 600/587 |
| 6,087,638 A | * | 7/2000 | Silverbrook | 219/540 |
| 6,209,386 B1 | * | 4/2001 | Mustacich et al. | 73/23.39 |
| 6,454,840 B1 | * | 9/2002 | Gellert et al. | 96/101 |
| 2002/0157951 A1 | * | 10/2002 | Foret et al. | 204/451 |

* cited by examiner

*Primary Examiner*—Robert H. Spitzer

(57) ABSTRACT

A separation column for a gas chromatograph that includes a block of electrically insulating material having a channel located between two strips of thermoelectric material spaced from the channel by strips of electrically insulating material. Electrodes are connected to opposite ends of the strips of thermoelectric material. More specifically, each strip of thermoelectric material has two layers of dissimilar material to enable the strips to provide selective heating and cooling depending on the direction of current flow through the strips.

19 Claims, 2 Drawing Sheets

SEPARATION COLUMN FOR A GAS CHROMATOGRAPH

CROSS-REFERENCE TO RELATED APPLICATIONS

Not Applicable

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

The present invention relates generally to an improvement in a gas chromatograph and specifically to the separation column portion of the gas chromatograph.

A gas chromatograph (GC) is an analytical instrument that takes a gaseous sample, and separates the sample into individual compounds, allowing the identification and quantification of those compounds. The principal components of a typical gas chromatograph are the following: an injector that converts sample components into gases, and moves the gases onto the head of the separation column in a narrow band; a separation column (typically a long, coiled tube) that separates the sample mixture into its individual components as they are swept through the column by an inert carrier gas, the separation being based on differential interactions between the components and an immobilized liquid or solid material within the column; a detector that detects and measures components as they exit the separation column; and a data display.

Typical modern GC instruments are configured with a heated-block "flash evaporator" type injector, a long capillary tube column, an oven housing the column to maintain and to change the column's temperature in a predictable and reproducible fashion, a detector, and a computer with dedicated hardware/software to process the data collected. Conventional GC instruments can be modified by using different columns (different lengths, different inner diameters, different sorbent phases, and different phase thickness); different detectors; and different data management systems.

Gas chromatographs are used to measure various gas or vaporizable species in a gas or liquid sample. A portion of the gas or liquid sample is received in an inlet of the gas chromatograph. The gas sample is moved through a column which has an interior that is lined with one of any number of known materials, depending on the particular application or gas chromatograph being used, the column separates the larger and smaller molecules in the gas sample. Thus, the gas sample exits the column in such a manner that the first gas species out of the column is the one with the smallest and lightest molecules (a typical example is helium), while the last species is the one with the largest and heaviest molecules. The length of the column varies with each application. Typically, however, where there are a large number of species which the chromatographer desires to separate out from a single gas sample, the column must be quite lengthy.

The gas exiting the column is directed to a detector which detects the various gas species in the sample, as they exit the column. The detector, in turn, provides an output signal indicative of those gas species. The different sample components are therefore retained for different lengths of time within the column, and arrive at the detector at characteristic times. These "retention times" are used to identify the particular sample components, and are a function of the type and amount of sorbtive material in the column, the column length and diameter, the carrier gas type and flow rate, and of the column temperature. In order to have repeatable retention times, the column temperature must also be repeatable. Because a gas chromatograph must operate in a range of ambient temperatures, the gas chromatograph must be controllably heated or cooled.

The current, widely used state of the art in capillary gas chromatography utilizes a gas chromatograph (GC) with an oven that heats a polyimide or metal clad fused silica tube coated with a variety of coatings (mostly polysiloxane based coatings). The oven uses a resistive heating element and a fan circulates heated air in the oven that is integrated into the GC and not the column. The column is cooled by opening vents in the oven, turning off the resistive heating element, and using forced air cooling of the column with ambient air or cryogenic coolent such as liquid carbon dioxide or liquid nitrogen. The disadvantage to the oven heating and cooling technology is that much more mass that is not central to the chromatographic process is heated and cooled than is necessary. Only the column (and the sample introduction and detection devices attached to the inlet and outlet of the column) need to be heated, and generally only the column needs to be cooled. As such, the current state of the art wastes energy, and is limited in its practical heat up (25–75° C./min) and cool down rates due to all the extra mass (oven walls, column hangers) that needs to be heated and cooled. Additionally, oven and column cool down rates slow exponentially the closer you get to ambient temperature if using ambient air to cool the oven. It also heats up the environment when cooling, resulting in additional air conditioning costs for laboratories. Alternatively, faster cooling and sub-ambient beginning temperatures can be achieved using cryogenic oven cooling, but this results in additional cost from the consumption of cryogen.

An alternative technology utilizes a metal sheath of unknown composition and resistance to heat a capillary GC column. The column is threaded into the metal sheath, and then the sheath is resistively heated during the chromatographic process, resulting in more rapid heating rates (20° C./sec) and more rapid cooling, because of the lower mass that needs to be heated and cooled relative to the oven heating technology described above, with significant efficiency gains ($1/20^{th}$ of the analysis time). The technology is currently marketed under the name EZ Flash™. U.S. Pat. No. 5,808,178 makes specific reference to resistive heating of a column within a sheath that is separate from the column, not actually integrated into the column structure.

U.S. Pat. No. 5,601,785 makes reference to a connector that would interface with a cartridge column, but the cartridge column is actually a conventional capillary encased in a smaller oven space.

U.S. Pat. No. 5,856,616 is similar to U.S Pat. No. 5,601,785 and the column is also separate from the heating device (a sleeve).

In U.S. Pat. No. 6,068,604, there is mention of a cartridge column and a column on a microchip with a heater attached to the outside of the column. There is no mention of incorporating the heating mechanism into the substrate of this chip in this patent, no mention of how to connect two halves.

Counter flow, gradient heating is as described in U.S. Pat. No. 4,923,486.

In addition to the capital cost of the heating and cooling components of prior art chromatographs, the components are expensive to run. Also, considerable time is required from changing from the heating mode to the cooling mode and back to the heating mode. These and other difficulties experienced with the prior art chromatographs have been obviated by the present invention.

It is, therefore, the principal object of the invention is to provide a separation column for a gas chromatograph which has an integral resistive heating component.

Another object of the present invention is to provide a separation column for a gas chromatograph which has an integral resistive heating and cooling component.

A further object of the present invention is to provide a separation column for a gas chromatograph which has a heating or a heating/cooling component which is relatively simple, relatively inexpensive to operate and is capable of changing temperature quickly and efficiently.

Still further objects of the invention are methods of making a separation column that has an integral resistive heating or resistive heating/cooling components.

BRIEF SUMMARY OF THE INVENTION

A separation column for a gas chromatograph that includes a block of electrically insulating material having a channel located between two strips of thermoelectric material spaced from the channel by strips of electrically insulating material. Electrodes are connected to opposite ends of the strips of thermoelectric material. More specifically, each strip of thermoelectric material has two layers of dissimilar material to enable the strips to provide selective heating and cooling depending on the direction of current flow through the strips.

BRIEF DESCRIPTION OF THE DRAWINGS

The character of the invention, however, may be best understood by reference to one of its structural forms, as illustrated by the accompanied drawings, in which.

DETAILED DESCRIPTION OF THE INVENTION

Figure 1:
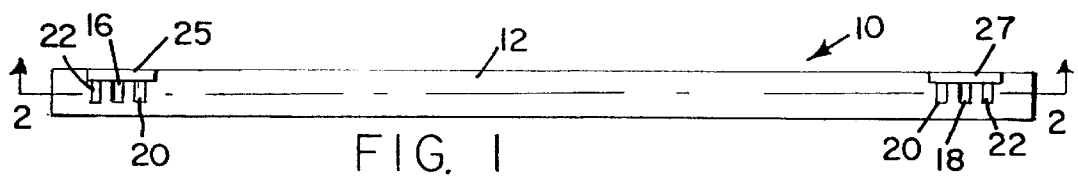
FIG. 1 is a top plan view of separation column embodying the principals of the invention.
Figure 2:
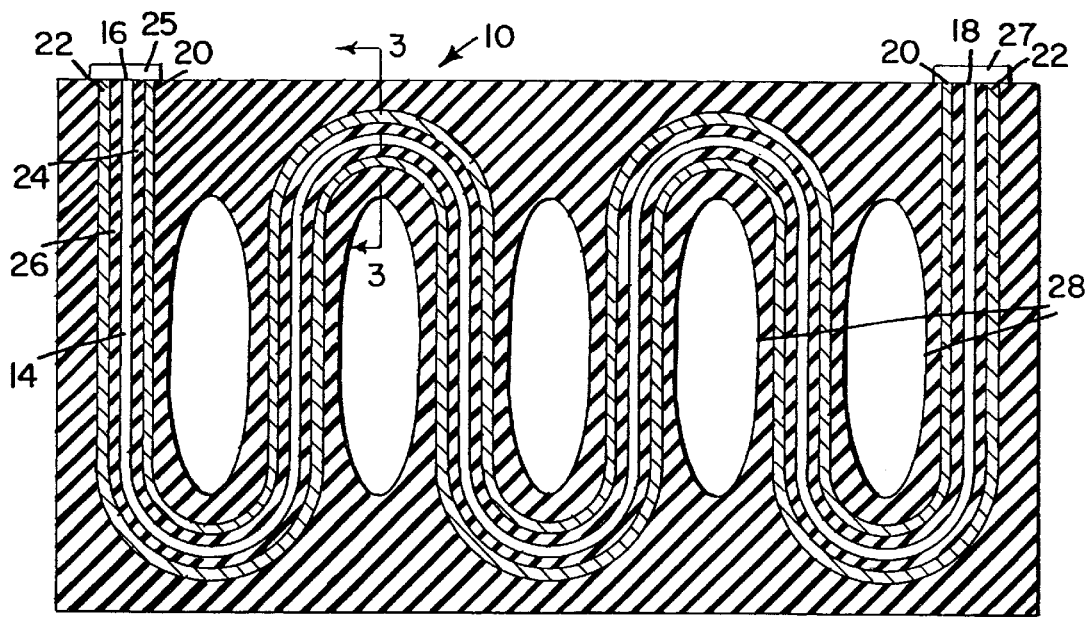
FIG. 2 is a vertical cross-sectional view taken along line 2—2 of FIG. 1, and looking in the direction of the arrows.
Figure 3:
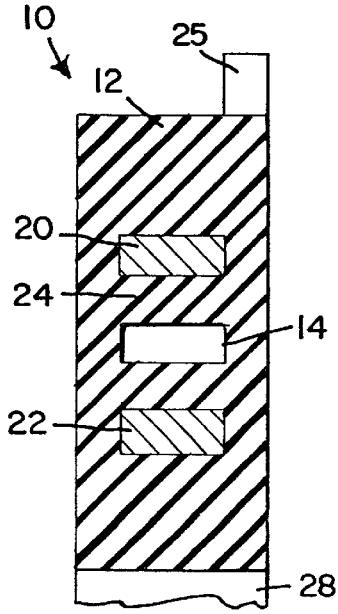
FIG. 3 is a vertical cross-sectional view taken along line 3—3 of FIG. 2, and looking in the direction of the arrows.

Referring first to FIGS. 1–4 there is shown a gas chromatography column embodying the principles of the present invention and generally indicated by the reference numeral 10. Column 10 comprises a block 12 of electrically insulating material that has a serpentine or sine wave shaped channel 14 that extends from an inlet opening 16 at the inlet end of the separation column through an exit opening 18 at the exit end of the separation column. The channel 14 is located between a first strip 20 of thermoelectric material and a second strip 22 of thermoelectric material. The strips 20 and 22 are separated from the channel 14 by first and second strips of electrical insulating material 24 and 26, respectively. The block 12 also has relatively large apertures 28 located between each loop of the channel 14 to reduce thermal mass. An electrode 25 is connected to the ends of the strips 20 and 22 at the inlet opening 16. Electrode 27 is connected to the opposite ends of the strips 20 and 22 at the exit opening 18. Electrodes 25 and 27 enable an electric current to be passed through the strips 20 and 22 to provide resistive heating of the strips 20 and 22 for heating the channel 16. Cooling of the block 12 and channel 16 is accomplished by any conventional cooling mechanism, such as fans, etc.

The first electrode 25 has a negative polarity and the electrode 27 has a positive polarity. When the electrodes 25 and 27 are connected to a source of electrical power to cause resistive heating of the strips 20 and 22, the strips are progressively hotter from the outlet opening 18 to the inlet opening 16. This is counter to the flow of gas which is from the inlet opening 16 to the outlet opening 18.

Figure 4:
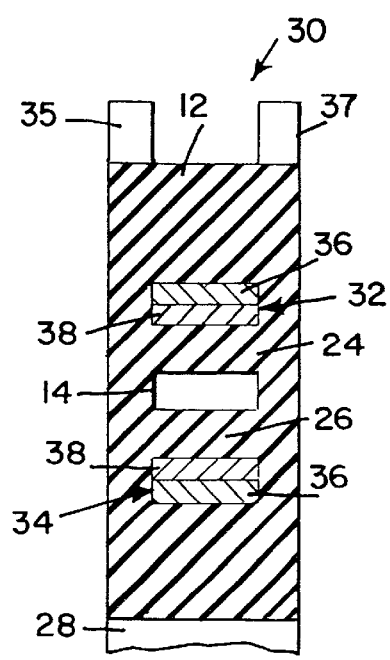
FIG. 4 is a view similar to FIG. 3 and showing a modification of the thermoelectric strip.

Referring to FIG. 4, there is shown a modified separation column, generally indicated by the reference numeral 30. Column 30 is identical to column 10 in every respect except that the channel 14 is located between first and second strips 32 and 34, respectively, of thermoelectric material. Each of the strips 32 and 34 has two layers 36 and 38 of dissimilar thermoelectric material. The layers 36 are of the same material and the layers 38 are the same material. Each layer 36 faces away from the channel 14 and each layer 38 faces the channel 14. A pair of electrodes 35 and 37 are connected to the strips 32 and 34 at the entrance end of the block 12. A pair of electrodes 35 and 37 are connected to the strips 32 and 34 at the exit end of the block 12. Electrodes 35 have a negative polarity. Electrodes 37 have a positive polarity. The layers of the strips 32 and 34 are adapted to produce a Peltier effect when an electrical current is caused to flow through the strips. When electrode 35 at the inlet end and electrode 37 at the outlet end are connected to a source of electrical power current flow through strips 32 and 34 is in a first direction. When electrode 35 at the outlet end and electrode 37 at the inlet end are connected to source of electrical power, current flow through strips 32 and 34 is in a second and opposite direction. The Peltier effect is produced when an electric current of magnitude I across the junction of two different conductors A and B with Peltier coefficients $II_A$ and $II_B$ produces heat at the rate $$W = (II_A - II_B) \cdot I$$

The sign of W can be positive as well as negative. A negative sign means cooling of the junction. Contrary to Joule heating, the Peltier effect is reversible and depends on the direction of the current.

The Peltier effect is caused by the fact that an electric current is accompanied by a heat current in a homogeneous conductor even at constant temperature. The magnitude of this heat current is given by $II \cdot I$. The peltier heat equation is the balance of the heat flows towards and away from the interface. The heat current accompanying the electric current is explained by the different flow velocities of the electrons carrying the electric current. The flow velocities depend on the energies of the conduction electron. E.g., even if the flow velocity of electrons of an energy above the chemical potential (Fermi energy) is higher than for electrons with a lower energy, the electric current is accompanied by a heat current in the opposite direction (since the electronic charge is negative). In this case the Peltier coefficient is negative. The same situation occurs for a $^n$-doped semiconductor, in which the electric current is carried by electrons in conduction-band states. The Seebeck and Peltier coefficient Q and Π obey the relation $$\Pi = T \cdot Q,$$

found already by Lord Kelvin, but for which a valid derivation could be given only later using the kinetic theory of conduction electrons or irreversible thermodynamics. The Kelvin relation connects the material constants for two very different physical effects, of which the Peltier effect has the explanation sketched above. When electrodes 35 and 37 are connected to a source of electrical power, heat flow from layers 36 to layers 38 to cause heating of the channel 14. When cooling the channel is desired, current flow is reverse by connecting electrodes 35' and 37' thereby, causing heat to flow from layers 38 to layers 36 and drawing heat away from the channel 14, thereby cooling the channel 14. In the heating phase, the temperature gradient is counter to the direction of the gas flow from the inlet opening 16 to the outlet opening 18 (cooler toward the exit end 18). Cooling can be further enhanced by also applying fan cooling. This maintains a temperature differential between the two layers 36 and 38, and accelerate the cooling of the channel 14.

Figure 5:
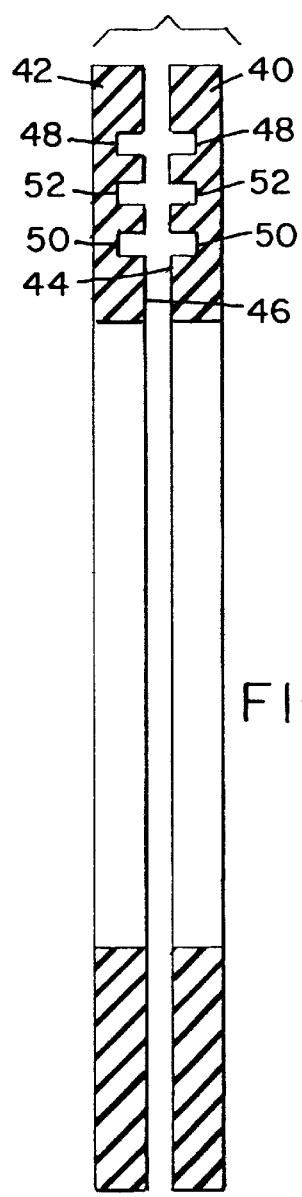
FIG. 5 is a vertical cross-sectional view illustrating one method of forming the separation column of FIGS. 1–3.

Referring to FIG. 5, there is illustrated a method of making block 12. The block 12 is formed by providing two identical half portions 40 and 42. The first half portion 40 has a first planar surface 44. The second half portion 42 has a second planar surface 46. Each of the planar surfaces 44 and 46 has a central groove 52 located between a first outer groove 48 and a second outer groove 50. The half portions 40 and 42 are brought together so that the planar surfaces 44 and 46 abut and these two surfaces are fixed, i.e., by gluing or welding. The channels formed by the grooves 48 and 50 are filled with a molten thermoelectric material which is allowed to harden. If the thermoelectric material is metal, the half portions 40 and 42 are made up of a material that is electrically insulating and which can withstand the heat of the molten metal which is used to fill the channels formed by the grooves 48 and 50. The block 12 will maintain its structural integrity and shape in the presence of molten metal. Also, instead of metal, a conductive ceramic can be used that has a coefficient of expansion more similar to fused silica and that "cures" once it is injected into the channels formed by the grooves 48 and 50, simplifying the filling process. When an electrically conductive ceramic is used, the half portions 40 and 42 can be made of a variety of materials, including plastic.

Figure 6:
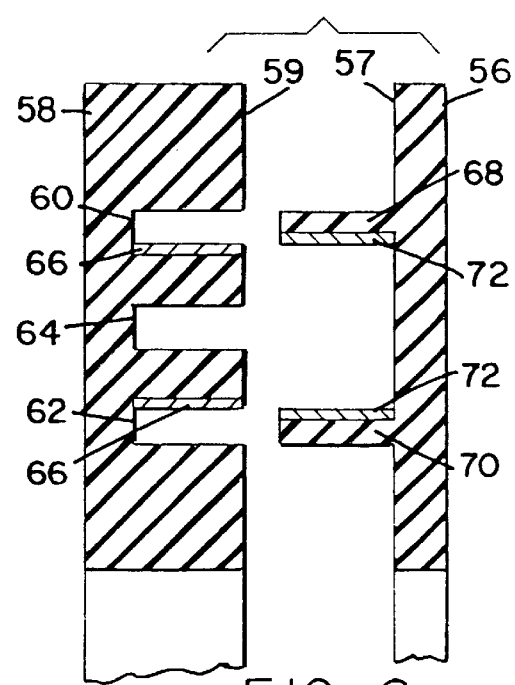
FIG. 6 is a vertical cross-sectional view illustrating a first method of forming the separation column of FIG. 4.

Referring to FIG. 6, the block 12 can also be made by providing two dissimilar half portions 56 and 58. Portion 56 has a planar surface 57 and two spaced ridges 68 and 70 extending transversely from the surface 57. Portion 58 has a planar surface 59 that contains a central groove 64 located between the first outer groove 60 and a second outer groove 62. The two half portions 56 and 58 are made of silica and made using a photolithographic technique. A coating of metal 72 is deposited on the sides of the ridges 68 and 70 that face each other and layers 66 on the surfaces of the grooves 60 and 62 that face away from the central groove 64. The layers 66 and 72 can be the same thermoelectric metal to form the embodiment of FIG. 3 or the metal can be dissimilar to form the embodiment of FIG. 4 for providing the Peltier effect. The first and second blocks 56 and 58, respectively, are brought together so that planar surfaces 57 and 59 abut and the ridges 68 and 70 enter the grooves 60 and 62 so that the layers 72 abut the layers 66 and the surface 57 is fixed to the surface 59 using Anodic welding. Alternatively, the surfaces 57 and 59 can be attached using a "glue" depending on the substrate that fills connecting points which are also etched along the surfaces 57 and 59.

Figure 7:
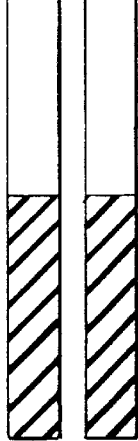
FIGS. 7–9 are vertical cross-sectional views illustrating a second method of forming the separation column of FIG. 4.
Figure 8:
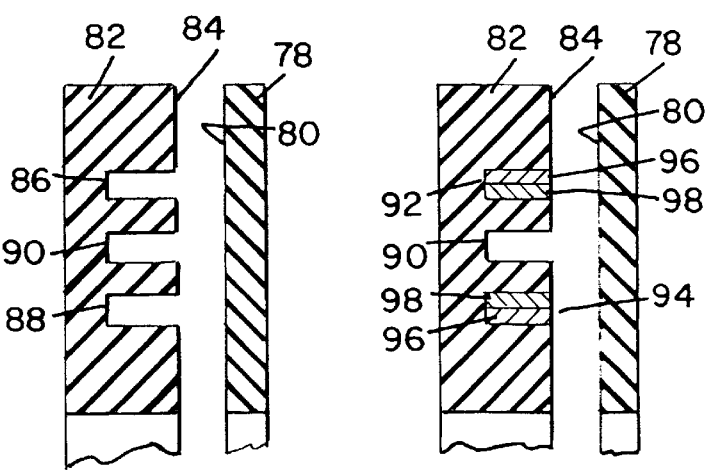
Figure 9:
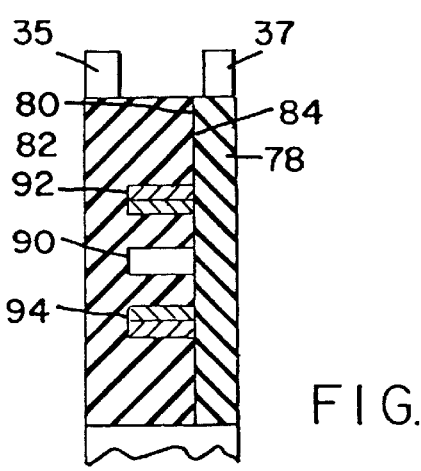

Referring to FIGS. 7–9, there is illustrated a still further method of making the block 12 by using two dissimilar blocks 78 and 82. Block 78 has a planar surface 80. Block 82 has a planar surface 84 that contains a central groove 90 located between a first outer groove 86 and a second outer groove 88. Referring to FIG. 8, a flexible strip of thermoelectric material, generally indicated by the reference numeral 92, is inserted into the groove 86. A similar strip of thermoelectric material, generally indicated by the reference numeral 94, is inserted into the groove 98. Each of the strips 92 and 94 can consist of a single homogeneous thermoelectric material such as metal to form the embodiment shown in FIG. 3 or, as in the example illustrated in FIG. 8, each of the strips 92 and 94 can be made up of two layers 96 and 98 of dissimilar thermoelectric material, adapted to produce the Peltier effect described above. The portions 78 and 82 are joined together so the face surfaces 84 and 80 abut and are fixed together by gluing or welding to produce the finished block shown in FIG. 9. The electrodes 35 and 37 are then added to each end of the combined blocks 78 and 82 for connecting the strips 92 and 94 to an electric current.

What is claimed is:

1. A method of heating a separation column for a gas chromatographic device comprising:
    (a) positioning a strip of thermoelectric material in contact with said separation column, said strip being adapted to produce a Peltier effect when an electric current is passed through said strip; and
    (b) passing an electric current through said strip selectively in a first direction to cause said strip to heat said separation column and in a second direction to cause said strip to cool said separation column.

2. The method as recited in claim 1, wherein said strip of thermoelectric material has a first layer of thermoelectric material that is positioned facing said separation column and a second layer of thermoelectric material which is different from said first layer and faces away from said separation column.

3. The method as recited in claim 1, wherein said separation column has a channel extending from an inlet opening to an outlet opening and a layer of electrically insulating material is positioned between said strip of thermoelectric material and said channel.

4. The method as recited in claim 1, wherein said separation column has a channel extending from an inlet opening to an outlet opening and said strip is a first strip and is located along a first side of said channel, said method further comprising positioning a second strip of thermoelectric material on a second side of said channel which is opposite said first side.

5. The method as recited in claim 4, wherein each of said first strip and said second strip comprises a first layer of thermoelectric material that faces said channel and a second layer of thermoelectric material which is different from said first layer and which faces away from said channel, said first and second layers being adapted to cause heat to be directed to said channel for heating said channel when an electric current is passed through said strip in said first direction, said first and second layers being adapted to cause heat to be absorbed from said channel and heat to be directed away from said channel when an electric current is passed through said strip in said second direction.

6. The method as recited in claim 5, wherein a first layer of electrically insulating material is positioned between said channel and said first strip and a second layer of electrically insulating material is positioned between said channel and said second strip.

7. A separation column for a gas chromatograph comprising:
   (a) a block of electrically insulating material, having an inlet opening at one end of said block, an outlet opening at the opposite end of the block and a channel extending from said inlet opening to said outlet opening;
   (b) a first strip of thermoelectric material from said inlet opening to said outlet opening along a first side of said channel;
   (c) a second strip of thermoelectric material from said inlet opening to said outlet opening along a second side of said channel, which is opposite said first side;
   (d) a first strip of electrically insulating material between said channel and said first strip of thermoelectric material;
   (e) a second strip of electrically insulating material between said channel and said second strip of thermoelectric material;
   (f) a first electrode connected to said first and second strips of thermoelectric material at said inlet opening; and
   (g) a second electrode connected to said first and second strips of thermoelectric material at said outlet opening, said first and second electrodes enabling the flow of an electric current through said first and second strips of thermoelectric material.

8. A separation column as recited in claim 7, wherein said thermoelectric material is metal.

9. A separation column as recited in claim 7, wherein said thermoelectric material is ceramic.

10. A separation column as recited in claim 7, wherein said channel has a serpentine form.

11. A separation column as recited in claim 10, wherein said serpentine form comprises a plurality of sinusoidal loops and said block has an aperture between each of said loops.

12. A separation column as recited in claim 7, wherein said first electrode has a negative polarity and said second electrode has positive polarity so that when an electrical current flows through said first and second strips of thermoelectric material, each of said first and second strips of thermoelectric material is progressively hotter from said outlet opening to said inlet opening.

13. A separation column as recited in claim 7, wherein each of said first and second strips of thermoelectric material comprises two layers of dissimilar thermoelectric material configured to produce a Peltier effect when an electric current is caused to flow through said strips of thermoelectric material, one of said layers facing said channel and the other of said layers facing away from said channel, said electrodes including a positive electrode and a negative electrode for enabling the flow of electric current through said first and second strips of thermoelectric material selectively in a first direction and in a second direction, flow of an electric current in said first direction causing heat to be absorbed from said channel and heat to be directed away from said channel for cooling said channel, flow of an electric current in said second direction causing heat to be directed toward said channel for heating said channel in accordance with the Peltier effect.

14. A method of making a separation column for a gas chromatographic device comprising the following steps:
   (a) forming a first block of electrically insulating material having an entrance end, an exit end, and a first planar surface face that extends from said entrance end to said exit end, said first planar surface having a first outer groove extending from said entrance end to said exit end, a second outer groove spaced from said first outer groove and extending from said entrance end to said exit end and a central groove between said first and second outer grooves and spaced from each of said first and second outer grooves;
   (b) forming a second block of electrically insulating material which is identical to said first block and includes a second planar surface that contains a first outer groove, a second outer groove, and a central groove;
   (c) fixing said first planar surface to said second planar surface so that the central groove of said first block is aligned with the central groove of said second block and each of the first and second outer grooves of said first block is aligned with respective first and second outer grooves of said second block, said first outer grooves forming a first outer channel, said second outer grooves forming a second outer channel and said central grooves forming a central channel;
   (d) filling each of said first outer channel and said second outer channel with a liquid thermoelectric material that is capable of changing from a liquid state to a solid state;
   (e) causing said thermoelectric material to change from said liquid state to a solid state to form a first strip of thermoelectric material and a second strip of thermoelectric material;
   (f) connecting a first electrode to each of said first and second strips of thermoelectric material at the entrance end of said first block; and
   (g) connecting a second electrode to each of said first and second strips of thermoelectric material at the exit end of said first block.

15. A method as recited in claim 14, wherein each of said first and second strips is metal and each of said first and second blocks is made of a material that is able to maintain structural integrity and shape when said metal is in a molten state within said central channel.

16. A method as recited in claim 15, wherein each of said first and second blocks is made of metal and each of said first and second outer channels is filled with a fluid ceramic material having thermoelectric properties and which is capable of changing to a solid state.

17. A method for making a separation column for a gas chromatograph device comprising the following steps:
   (a) forming a first block of electrically insulating material having an entrance end, an exit end, and a first planar surface face that extends from said entrance end to said exit end, said first planar surface having a first outer groove extending from said entrance end to said exit end, a second outer groove spaced from said first outer groove and extending from said entrance end to said exit end and a central groove between said first and second outer grooves and spaced from each of said first and second outer grooves, said first outer groove having a first outer surface that faces away from said second outer groove, said second outer groove having a second outer surface that faces away from said first outer grove, each of said first and second outer surfaces being transverse to said first planar surface;
   (b) forming a second block of electrically insulating material having an entrance end, an exit end and a second planar face that extends from said entrance end to said exit end, said second block having a first ridge and a second ridge spaced from said first ridge, each of said first and second ridges projecting transversely from said second planar face and extending from the entrance end to the exit end of said second block, the spacing between said first and second ridges being the same as the spacing between said first and second outer grooves, said first ridge having a first inner surface that faces said second ridge, said second ridge having an inner surface that faces said first ridge, each of said first and second inner surfaces being transverse to said second planar surface;

(c) fixing a layer of a first thermoelectric material on the inner surface of each of said first and second ridges;

(d) fixing a layer of a second thermoelectric material on the outer surface of each of said first and second grooves, said second thermoelectric material being different from said first thermoelectric material;

(e) joining said first and second blocks so that said first ridge enters said first groove, said second ridge enters said second groove, said first planar surface abuts said second planar surface, the entrance end of said first block is adjacent the entrance end of said second block, and the exit end of said first block is adjacent the exit end of said second block;

(f) fixing said first planar surface to said second planar surface;

(g) connecting a first electrode assembly to each of said layers at the entrance ends of said first and second blocks; and (h) connecting a second electrode assembly to each of said layers at the exit end of said first and second blocks.

18. A method of making a separation column for a gas chromatographic device comprising the following steps:

(a) forming a first block portion of electrically insulating material having an entrance end, an exit end, and a first planar surface face that extends from said entrance end to said exit end, said first planar surface having a first outer groove extending from said entrance end to said exit end, a second outer groove spaced from said first outer groove and extending from said entrance end to said exit end and a central groove between said first and second outer grooves and spaced from each of said first and second outer grooves;

(b) forming a second block portion of electrically insulating material having a second planar surface;

(c) inserting a first strip of a thermoelectric material in said first outer groove;

(d) inserting a second strip of thermoelectric material in said second outer groove; and (e) fixing said first planar surface to said second planar surface to form a block having a first strip of thermoelectric material, a second strip of thermoelectric material and a channel between said first and second strips and separated from said first and second strips by a layer of electrically insulating material.

19. A method as recited in claim 18, wherein each of said first and second strips comprises a first layer of a thermoelectric material that faces away from said channel and a second layer of thermoelectric material that faces said channel and is different from the thermoelectric material of said first layers.

\* \* \* \* \*